US00PP10468P

United States Patent [19]

van Andel

[11] Patent Number: Plant 10,468

[45] Date of Patent: Jun. 30, 1998

[54] FREESIA PLANT VARIETY NAMED 'VARAYEL'

[75] Inventor: Jacob van Andel, Aalsmeer, Netherlands

[73] Assignee: Van Staaveren B.V., Aalsmeer, Netherlands

[21] Appl. No.: 814,540

[22] Filed: Mar. 10, 1997

[51] Int. Cl.[6] ..... A01H 5/00

[52] U.S. Cl. ..... Plt./83

[58] Field of Search ..... Plt./83

[56] References Cited

U.S. PATENT DOCUMENTS

P.P. 9,293 9/1995 Van Andel ..... Plt./83
P.P. 9,294 9/1995 Van Andel ..... Plt./83

*Primary Examiner*—James R. Feyrer
*Assistant Examiner*—Kent L. Bell
*Attorney, Agent, or Firm*—Christie, Parker & Hale, LLP

[57] ABSTRACT

A new plant variety of freesia suitable for growing under glass as a cut flower.

1 Drawing Sheet

BACKGROUND OF THE INVENTION

This invention relates to a new and distinct variety of Freesia which originated by crossing two unpatented, unnamed varieties at the Van Staaveren Nursery in Aalsmeer, The Netherlands. The female parent is identified as 87316-AT1 and the male parent is identified as 87310AT4.

SUMMARY OF THE INVENTION

Among the features which distinguish the new variety from other presently available and known commercial cultivars are attractive flowers and early flowering response after planting which distinguishes the new variety as suitable for use as a cut flower variety. Asexual reproduction of the new variety by corms and cormlets in Aalsmeer, The Netherlands has established that the distinctive characteristics are transmitted through succeeding generations. The varietal denomination of the new variety is 'Varayel'.

Flowering Time

Under conditions of growing plants under glass in The Netherlands, Freesia plant varieties typically flower in about 22 to 23 weeks for plants planted in October; about 21 to 22 weeks for plants planted in December/January; and about 20 to 30 weeks for plants planted in June/July (flowering depends on soil temperature after about 20 to 30 weeks). In contrast to the above, the flowering time after planting for 'Varayel' is about 18 weeks, about 16 weeks and about 15 weeks for October planting, January planting and June planting, respectively, under glass in Aalsmeer, The Netherlands.

BRIEF DESCRIPTION OF ILLUSTRATION

The accompanying photograph illustrates the new variety and shows the flowering thereof from bud to full bloom depicted in color as nearly correct as it is possible to make in a color illustration of this character. Throughout this description, color values are based upon the Colour chart of The Royal Horticultural Society of London, England, except where common terms of color definition are employed.

DESCRIPTION OF THE NEW VARIETY

The following description is of plants of the new cultivar grown under glass in Aalsmeer, Netherlands, during the month of November. Phenotyphic expression may vary with environment, cultural and climatic conditions, as well as differences and conditions in light, soil, and temperature.

Plant:

A. *Form.*—Erect.

B. *Growth.*—Height attained: Medium. Branching: No.

C. *Flower stem.*—1. Length: Medium. 2. Color: Near 143A.

D. *Foliage.*—1. Quantity: Relatively small number of leaves. 2. Size: Length — about 100 cm. Width — about 1.5 cm. 3. Shape of leaf: Oblongate. 4. Texture: Leaf top side — smooth; leaf. underside — smooth. 5. Color: Leaf top side — near 141A; leaf. underside — near 141. 6. Veination: Yes, normal. 7. Stem color: Near 143A. 8. Corms: Color: White with brown scales. Size: Varying.

The bud stage:

A. *Bud form.*—Long ovate.

B. *Bud size.*—About 15 mm×45 mm.

C. *Opening rate.*—Medium.

D. *Color.*—1. When petals first divide: Near 12. 2. When petals begin to unfurl: Near 11A. 3. When flowers open: Inner petals: Near 11A top, near 12A bottom. Outer petals: Near 11A top, near 12A bottom. 4. Calyx: Shape: Tubular. Size: Small.

The flower stage:

A. *Inflorescence.*—1. Blooming habit: Intermittent. 2. Form: Cup. 3. Type: Raceme. 4. Diameter: About 45 mm×60 mm. 5. Approximate number of flowers: 7–9. 6. Response time: Early.

B. *Bloom.*—1. Type: Single. 2. Form: Intermittent. 3. Borne: Raceme. 4. Size (fully expanded): About 45 mm×60 mm. 5. Shape: Cup. 6. Color Tonality from a distance: Yellow. 7. Lasting quality on plant: Long, over 14 days.

C. *Flower color.*—1. Flower coloration: Yellow. 2. Inner petals: Near 11A. 3. Outer petals: Near 11A. 4. Point of petal attachment: Near 11A. 5 Discoloration as bloom ages: Slight discoloration (with stripes). 6. Petals: Number of petals: 6. Arrangement: Tubular. Texture: Soft. Shape: Broad elliptic. Color: Top near 11A, Underside near 11A.

D. *Persistance.*—About 18 days on plant; after cutting about 8 days.

E. *Fragrance.*—Slight.

Reproductive organs:

A. *Stamens, filaments and anthers.*— 1. Stamens: Double forked, white. 2. Anthers: 3 singles. Color: White with yellow base. 3. Filaments: White. 4. Pollen: White/yellow.

B. *Pistils.*—1. Styles: 3. 2. Stigmas: 1. 3. Character of ovaries: Cylindrical. 4. Calyx Shape: Funnel. Size: About 8–10 mm.

I claim:

1. A new and distinct variety of freesia plant substantially as described and illustrated herein.

* * * * *

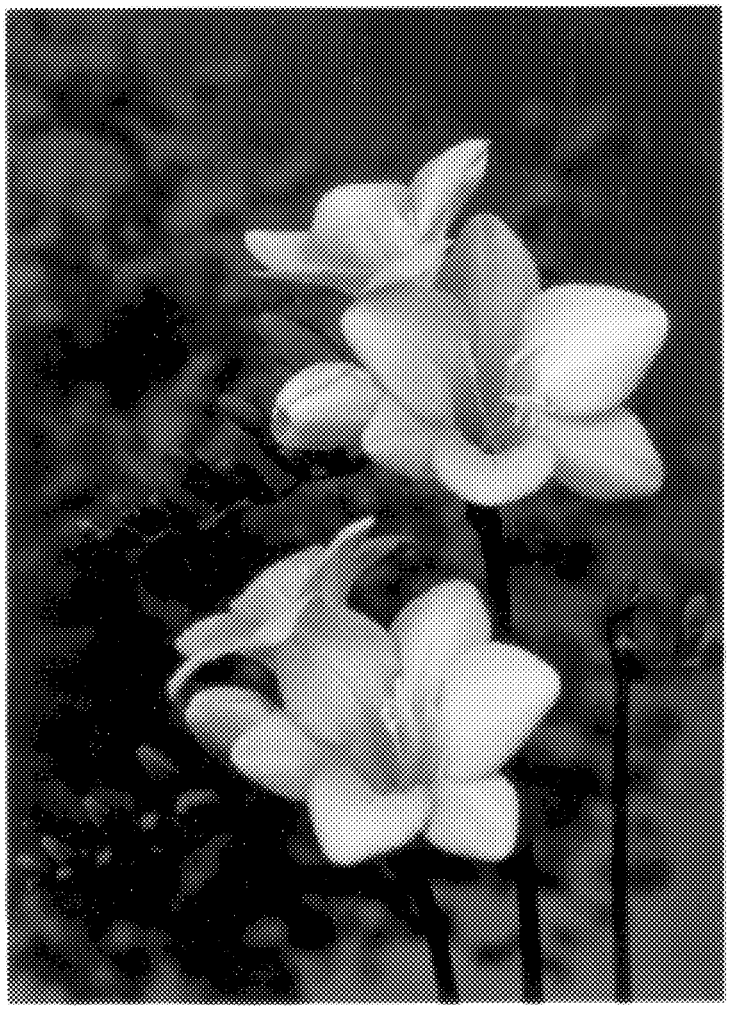

UNITED STATES PATENT AND TRADEMARK OFFICE

CERTIFICATE OF CORRECTION

PATENT NO. : Plant 10,468
DATED : June 30, 1998
INVENTOR(S) : Jacob van Andel

It is certified that error appears in the above-indentified patent and that said Letters Patent is hereby corrected as shown below:

Column 2, line 19, change "141" to -- 141A --.
Column 2, line 26, change "12" to -- 12A --.

Signed and Sealed this

Fifth Day of October, 1999

*Attest:*

Q. TODD DICKINSON

*Attesting Officer*

*Acting Commissioner of Patents and Trademarks*